United States Patent [19]

Hills

[11] Patent Number: 4,851,339

[45] Date of Patent: Jul. 25, 1989

[54] EXTRACTION OF ANTI-MUTAGENIC PIGMENTS FROM ALGAE AND VEGETABLES

[76] Inventor: Christopher B. Hills, 13155 Pine St., Boulder Creek, Calif. 95006

[21] Appl. No.: 846,724

[22] Filed: Apr. 1, 1986

[51] Int. Cl.[4] .............................................. C12P 23/00
[52] U.S. Cl. ........................................ 435/67; 435/946
[58] Field of Search .......................... 435/67, 257, 946

[56] References Cited

U.S. PATENT DOCUMENTS

| | | |
|---|---|---|
| P.P. 4,511 | 3/1980 | Avron et al. . |
| 2,848,508 | 8/1958 | Barnett et al. . |
| 3,268,606 | 8/1966 | Jaeger ................................... 435/67 |
| 3,790,688 | 2/1974 | Walter et al. . |
| 4,199,895 | 4/1980 | Avron et al. . |
| 4,320,050 | 3/1982 | Rebeller et al. ....................... 435/67 |
| 4,439,629 | 3/1984 | Ruegg . |

OTHER PUBLICATIONS

Krinsky, N. I. and Welankiwar, S. "Assay of Carotenoids" in *Method. Enzymol.* (1984) 105:185.

Primary Examiner—Barry S. Richman
Assistant Examiner—Timothy M. McMahon
Attorney, Agent, or Firm—Hamilton, Brook, Smith & Reynolds

[57] ABSTRACT

A method of extracting carotenoid, tetrapyrrole and porphyrin from vegetable sources of such pigments, especially algae, as described. The method entails production of water soluble and oil soluble extracts and includes an extractive procedure for rendering carotenoids water soluble. The pigment extracts can be used as nutritional or medicinal compositions.

11 Claims, 1 Drawing Sheet

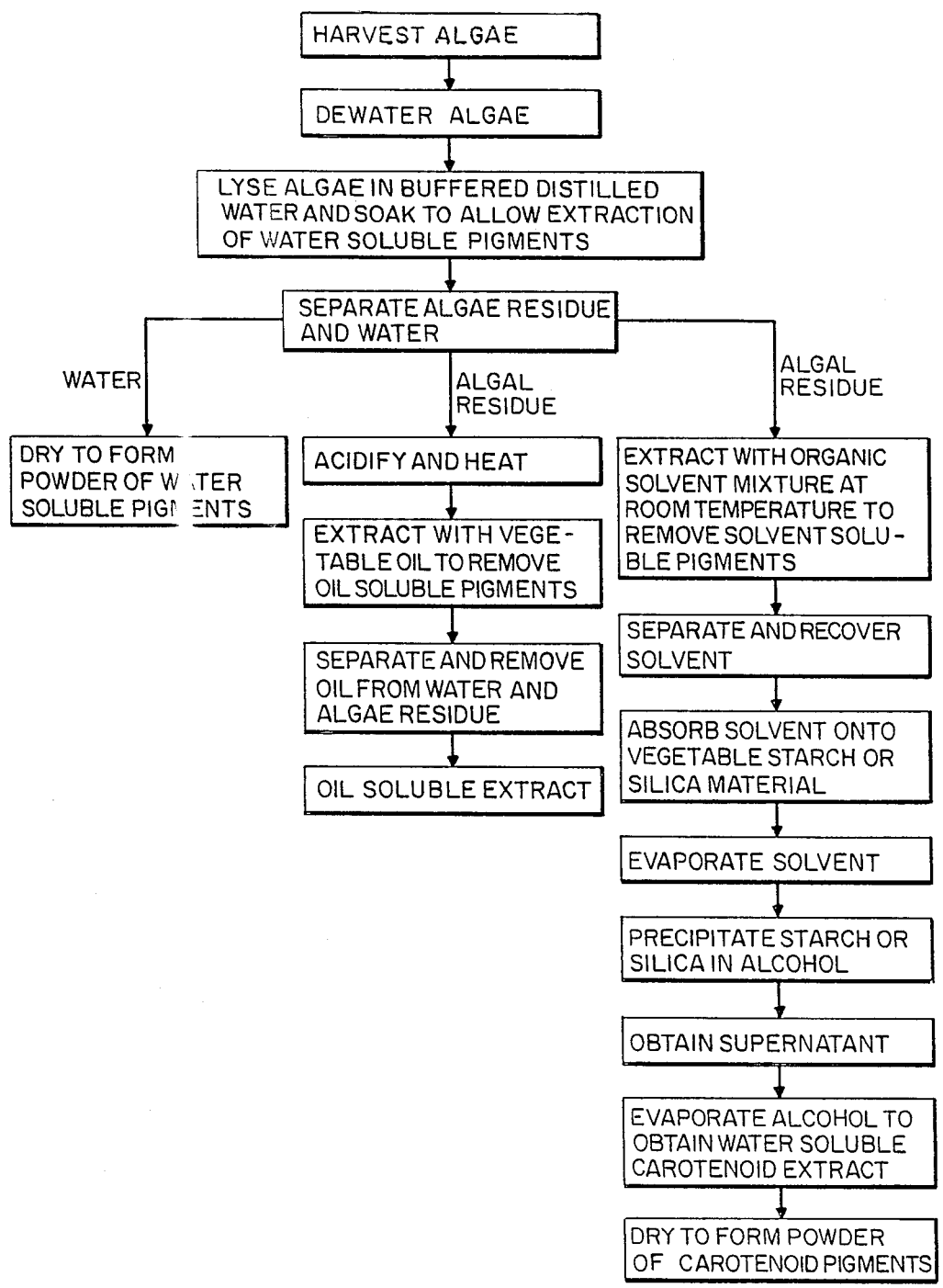

EXTRACTION OF ANTI-MUTAGENIC PIGMENTS FROM ALGAE AND VEGETABLES

FIELD OF THE INVENTION

This invention is in the fields of organic chemistry and biochemistry. The invention pertains to a procedure for extracting carotenoid, tetrapyrrole and porphyrin pigments from vegetable sources (especially algae).

BACKGROUND

Carotenoids are lipids which are soluble in organic solvents and can be extracted from tissues of plants and animals by polar solvents such as acetone and alcohols mixed with nonpolar solvents such as hexane, chloroform, ether, etc. Carotenoids are not directly soluble in water; in plants they are bonded in tissues and cells by fatty acids and oils and are present in colloid form with plant starches and polymers. Conventional methods of extraction and isolation of carotenoids are designed to separate carotenoid pigments from their natural protein starch complexes and from other plant pigments (such as porphyrins) and to isolate the carotenes separately. Use of organic solvents such as hexane, benzene, chloroform, acetone, ether and methanol or mixtures thereof for extraction of carotenoids from algae or other vegetables generally involves the removal of carotenoids from pulverized vegetable residues into the solvent, from which the carotenoids are then recovered by evaporation or distillation of the solvent. Various procedures have been developed to facilitate extraction of pure carotenoids.

In one method of extracting beta-carotene, for example, algae material is treated with calcium hydroxide and heated to a temperature of 50° C. to about 100° C. This results in conversion of chlorophyll present in the algae to calcium salts which are insoluble in the organic solvents used for beta-carotene extraction and as a result, chlorophyll pigments are absent from the final solvent extracted beta-carotene. See U.S. Pat. No. 4,439,629.

Efforts have also been directed toward providing water dispersible preparations of betacarotene. For example, a water dispersible preparation of beta-carotene has been prepared by adding beta-carotene to hot solutions of starch, then heating the mixture to temperatures of 100°–121° C. to stabilize the carotene. A food color with one absorption maxima of 520–530 nm can be made if pure synthetic betacarotene is used. See U.S. Pat. No. 3,790,688.

Beta-carotenoid in nature is always found associated with other pigments such as the tetrapyrroles and porphyrins (e.g., chlorophyll) and other carotenoids such as zeaxanthin and echinenone. Further, carotenes are present in membranes of animals and plants in carotenoid protein complexes called carotenoproteins. In conventional extraction procedures, these complexes are destroyed in the effort to obtain pure pigments.

DISCLOSURE OF THE INVENTION

This invention pertains to a method of extracting a wide complement of carotenoid, tetrapyrrole and porphyrin pigments from vegetable sources of such pigments, especially algae. The pigments are extracted so as to preserve the natural protein and/or starch complexes in which the pigments exist in vegetable cells. The invention constitutes a process for producing two types of extracts- a water soluble extract (containing water soluble tetrapyrroles and porphyrins and certain carotenoid pigments which have been rendered water soluble) and an oil soluble extract. These extracts either separately or combined, contain a wide spectrum of water soluble and water insoluble carotenoid and tetrapyrrole pigments. The types of carotenoid and tetrapyrrole pigments which can be extracted by the procedures of this invention is shown in Tables A and B below.

TABLE A

| Carotenoid | Merck No. | Chemical Formula | Molecular Weight |
|---|---|---|---|
| Carotene(alpha) | 1836 | $C_{40}H_{56}$ | 536.85 |
| Carotene(beta) | 1837 | $C_{40}H_{56}$ | 536.85 |
| Carotene(gamma) | 1838 | $C_{40}H_{56}$ | 536.85 |
| Lycopene | 5436 | $C_{40}H_{56}$ | 536.85 |
| Phytofluene | 7272 | $C_{40}H_{62}$ | 548.94 |
| Echinenone | 3475 | $C_{40}H_{54}O$ | 550.8 |
| Cryptoxanthin | 2598 | $C_{40}H_{56}O$ | 552.85 |
| Lycoxanthin | 5443 | $C_{40}H_{56}O$ | 552.85 |
| Rubixanthin | 8153 | $C_{40}H_{56}O$ | 552.85 |
| Canthaxanthin | 1729 | $C_{40}H_{56}O_2$ | 564.82 |
| Lycophyll | 5437 | $C_{40}H_{56}O_2$ | 568.85 |
| Xanthophyll | 9875 | $C_{40}H_{56}O_2$ | 568.85 |
| Zeaxanthin | 9920 | $C_{40}H_{56}O_2$ | 568.85 |
| Neoxanthin | — | $C_{40}H_{56}O_4$ | 600 |
| Violaxanthin | 9801 | $C_{40}H_{56}O_4$ | 600.85 |
| Myxoxanthophyll | — | $C_{46}H_{66}O_7$ | 730 |

TABLE B

| Tetrapyrrole and porphyrin pigments | Merck No. | Chemical Formula |
|---|---|---|
| Chlorophyll(a) | 2128 | $C_{55}H_{72}MgN_4O_5$ |
| Chlorophyll(b) | 2128 | $C_{55}H_{70}MgN_4O_6$ |
| Chlorophyll(d) | 2128 | $C_{54}H_{70}MgN_4O_6$ |
| Chlorophyllin | 2128 | $C_{34}H_{31}N_4Na_3MgO_6$ |
| Pheophytin | 2128 | $C_{55}H_{72}FeN_4O_5$ |
| Protoporphyrin IX | 7800 | $C_{34}H_{34}N_4O_4$ |
| Pychoerythrin | 7263 | $C_{31}H_{38}O_2N_4$ |
| Pychocyanin | 7263 | $C_{31}H_{38}O_2N_4$ |
| Phytochlorin | 7271 | $C_{34}H_{36}N_4O_6$ |

The water-soluble extract is a composite of two extracts- a water extract of water soluble pigments (such as phycocyanin) and a preparation of solvent-extracted water insoluble pigments (such as carotenoids) rendered water soluble.

Extracts of water soluble phycocyanin and other porphoryins are obtained by directly extracting these pigments from the vegetable source with water. The vegetable material is extracted with distilled water, initially, for several hours at room temperatures and then, further, in the cold for about 2 weeks. After extraction, the water containing the water soluble pigments is separated from the vegetable residue by, for example, filtration and any remaining algae particles are sedimented out by centrifugation. The water extract can be dried to form a powder of the extracted pigments.

The process for rendering carotenoids water soluble to produce a water soluble carotenoid preparation is performed as follows. The vegetable matter containing the carotenoids (freshly obtained vegetable matter or the residue from water-extracted vegetable matter) is extracted with an organic solvent in which carotenoids are soluble. A preferred solvent for this extraction is a mixture containing about 3 parts chloroform, 2 parts hexane, 1 part ether and 1 part methanol. After extraction, the solvent is separated from the vegetable material, generally by filtration or centrifugation. The solvent containing the extracted pigments is then absorbed into a pregelatinized starch/protein powder (e.g., Instant gel TM, Staley, Inc.) or a silica resin. This can be accomplished by spraying or by pouring the solvent onto a bed of the starch/protein gel or of silica granules. The solvent is then evaporated and the starch/protein granules or silica granules containing the pigments are precipitated in alcohol. The precipitate is settled and the supernatant is obtained. The supernatant is then reconstituted into a carotene polymer with the addition of absolute alcohol. The resulting colloid suspension is water-soluble which can be dried and stored without loss of potency. This water-soluble carotenoid preparation can be combined with the water extracted porphyrins and tetrapyrroles to produce a composite water-soluble preparation of vegetable pigments.

The procedure for preparing an oil extract of oil soluble products is performed by homogenizing or otherwise disintegrating vegetable cells in a vegetable oil such as soy, palm, corn or fish oil or by adding oil to a dewatered preparation of disintegrated vegetable cells. An emulsion is formed which is acidified (about pH 2.5) with a food grade acid and then heated. Extraction is allowed to proceed after which the mix is cooled to room temperature. The oil is separated from water and solids by centrifugation. The oil containing other pigments is then recovered.

The plant pigment extracts prepared by the method of this invention can be used as a food or dietary supplement or a medicinal preparation of carotenoid, tetrapyrrole, and porphyrin pigments.

BRIEF DESCRIPTION OF THE FIGURE

The FIGURE is a scheme outlining a preferred embodiment of the invention.

BEST MODE FOR CARRYING OUT THE INVENTION

The method of this invention can be used to extract the plant pigments set forth in Table A and B from any vegetable source of these materials. Depending on the content of the vegetable source, extracts containing all or some of these pigments can be prepared. The preferred sources of these pigments for application of the extractive procedures of this invention are algae, particularly algae of the genera Spirulina and Dunaliella. (e.g., *D. bardawil* and *D. salina*) Algae of these genera can-be readily cultivated to provide an ample source of the pigments.

A preferred embodiment for preparing the water soluble and oil soluble extracts from algae is set forth schematically in the FIGURE. According to this embodiment, the water and oil extract can be made from a single batch of algae material. Alternatively, each extract can be formed de novo from separate batches of algae.

Algae to be extracted is harvested and dewatered. The algae material is then immersed in buffered, distilled water at 25° C. to lyse algae cells. The resulting suspension of algae material is kept in the cold (refrigerated) for a time sufficient to allow extraction of water soluble materials. Preferably, the extraction is allowed to proceed for about 2 weeks. The residue of algae material is then removed from the water extract, for example, by filtration or by allowing the algae material to settle and by siphoning off the water. The water supernatant containing water soluble pigments is thus obtained. This can be further purified by centrifugation and dialyzed and sterilized. The preparation can be dried to provide a powder of water soluble material.

The algae residue remaining after water extraction can be used to produce a water-soluble carotenoid extract and an oil extract. (Alternatively, the extract can be prepared from fresh algae). To prepare the water soluble carotenoids, a portion of the residual algae material is dewatered and then extracted with an organic solvent for carotenoid removal. The solvent can be a mixture of organic solvents comprising a non-polar solvent or solvents (e.g., hexane, chloroform) and optionally a polar component (e.g., an alcohol). Applicant has discovered that a particular mixture of solvents, namely chloroform:hexane:ether and methanol in proportions of about 3:2:1:1, provides extraction of an exceptionally large yield of pigments and associated material. (See below) Thus, this particular mixture of solvents is preferred.

The extraction is performed at room temperature. Heating significantly above room temperature is avoided so as not to alter the natural isomer mix of carotenoids.

After extraction, the solvent and algae residue are separated, generally, by filtration. The solvent containing this carotenoid pigments is then applied to a starch material or a silica material. A preferred material is a vegetable starch such as a corn starch in pregelatinized form. A particularly preferred starch material is a pregelatinized corn starch sold under the trademark Instant Gel TM by Staley, Inc. The solvent can be applied to the starch material by spraying. After this is applied and absorbed into the starch base, the solvent is allowed to evaporate. The dried starch material is then precipitated in alcohol to yield a supernatant containing a water-soluble carotenoid material. The supernatant is separated and the resulting preparation can be dried for storage or combination with the water extracted pigment preparation.

The oil extract is prepared by extracting the algae residue in a vegetable oil (e.g., corn oil). Algae residue (from the initial water extraction procedure) is acidified (pH 2.5) with a food grade acid. Oil is then added and the resulting emulsion is heated to about 70° C. Extraction is performed for about 2 hours after which the oil is separated to yield an extract of oil soluble pigments.

A particularly preferred mode of carrying out the entire extractive process for Spirulina algae is set forth in detail below.

1. An algae-growing pond is inoculated with about 200,000 cells/ml$^3$ (or 0.175 optical density) of an algae culture. The algae is cultivated in the pond system until it reaches an optical density of about 0.6–0.7 (400,000–800,000 cells/ml$^3$). Carbon dioxide can be passed through the pond culture to enhance algae growth rate.

2. The water-soluble extract of Spirulina algae is produced by lysing and soaking the algae in cold, distilled water containing a buffer (pH 6–8) for about 2 weeks. The algae material is removed by filtration and centrifugation. The water extract so obtained is dried to form a powder which can be combined with oil soluble pigments rendered water soluble by the process of steps 11 and 12.

3. For extraction of the oil soluble pigments, flocculation is produced with potassium alum or alum sulphate, and a polymer monomer is added depending on the concentration of the algae.

4. If dry, powdered algae is required at this stage, the wet algae is desalted by ultrafiltration and microfiltration, and concentrated in a centrifuge. The resulting paste is vacuum-dried or freeze-dried.

5. If the oil-extract process is desired, the algae passes from the flocculation tank to a kinetic screen for dewatering.

6. Carotenes are transferred from the algae to an oil solvent by the algae in a pH-adjust tank to pH 2-2.5. The algae is then homogenized, and circulates through to a heating tank which remains at 70° C. for two hours in a jacketed tank.

7. The heating tank is then cooled with a chiller to reach room temperature within one-half hour.

8. The algae mix is separated in a holding tank until the oil separates from the settled algal material and the remaining salt water.

9. The emulsion and supernatant are then passed through an oil or cream separator centrifuge for concentration of the oil solution containing betacarotene and other oil-soluble carotenoids.

10. The oil is then packaged in nitrogen or inert-gas-filled containers, where the carotenes remains stable and ready for use.

11. To develop a water-soluble product from this oil solvent, the oil solvent is mixed with a mixture of chloroform, hexane, ether, and methyl alcohol (3:2:1:1). This mixture is then evaporated and dried at low temperature onto a starch/protein base.

12. The starch/protein base is precipitated in absolute alcohol. The supernatant becomes a water soluble polymer ready for use as a concentrate which contains 4-5% carotenes.

The extractive procedure of this invention is designed to produce a series of extracts containing concentrated amounts of carotenoid, tetrapyrrole and porphyrin pigments without altering the natural complexes and combinations in which the pigments exist in the plant cell source. For example, the method of producing a water soluble carotenoid preparation avoids the use of heat which can cause interconversion of carotene isomers. Further, this extractive procedure does not eliminate protein amino acids and it does not dissolve the plant starch or fatty acids in order to cleave the protein and starch bonds, which would normally achieve a purer extract of the carotene component. As mentioned, conventional methods of extraction and isolation are designed to separate the carotenoid pigments from their protein starch complex and then to isolate the carotenes separately from the solvent. The process of this invention enables various isomers of the carotenoid pigments to be retained in the extract in conjugation with the amino acids in proteins and starch colloids in a soluble form. This procedure enriches the pigments interactively by keeping them associated with each other as they are found in nature.

In the process of producing a water soluble carotenoid extract, the pigment/protein-starch complexes are extracted and dried onto an instant starch substrate without purification or distillation. Thus, the process is one of evaporation of the solvent to leave behind the starch-protein complexes along with the carotenoids extracted. Employing this method the natural isomers of beta-carotene have been extracted from Spirulina and Dunaliella algae, and have been determined to be a mix of all-trans, 9-cis and 15-cis with approximately 40% of unidentified isomers.

Carotenoids divided from their natural colloid state in plant lipids and starches are unstable, as they are highly oxidatable in both light and air when extracted by solvents. However, when extracted by the preferred mixture of organic solvents of this invention and then dried onto a dry plant starch, carotenes become not only stable, but water-dispersible as in nature. The final product extracted can be membrane filtered by reverse osmosis to remove any particulates and then sterilized.

The present invention includes the extraction of the carotenoid myxoxanthophyll from the mucopolysaccharide cell walls of the algae, in order to combine this rhamnoside-based carotenoid with water-soluble protein macromolecule complexes such as copperpheophytin, cobalt-phycocyanin, and magnesium-chlorophyll extracted from the Spirulina. These extracts also contain iron-haem proteins, the non-haem ironsulphur protein ferrodoxin, and the flavo-protein enzyme ferredoxin-NADP; there are also extracted and bonded to a soluble starch polymer by the method of this invention, and are considered important in the interactive function of cytochromes and the oxygen transporting blood pigment of most animals.

Saponification by treating algae with hydroxides employed in some current extraction methods destroys chlorophyll and other porphyrin pigments by removing the magnesium or central atom from the molecule, so that the water-soluble chlorophyll degradation products and other porphyrin degradation products are easily washed out of the extract. By the procedure of this invention, these extracted derivatives are preserved, relatively stable, easy to handle, and easily identified in the total complex by their spectral absorption maxima. For instance, an important shift from the pheophytin to pheophorbide is avoided in the extraction process through the use of a mild, harmless food-grade acid instead of an alkaline saponification agent (such as the calcium hydroxide used in U.S. Pat. No. 4,439,629).

The preferred solvent used for extraction of pigments for preparation of the water-soluble carotenoid extract is a mixture of polar and nonpolar organic solvents comprising chloroform, hexane, ether and methanol in a ratio of about 3:2:1:1. The mixture provides a high yield of pigments. Table C shows a comparison of Spirulina extracts prepared by extraction with hexane (Extract A), chloroform: hexane 3:1 (Extract B) and chloroform:hexane:ether: methanol 3:2:1:1 (Extract C). The amount of pigments removed by Extract C is significantly greater than that removed by either Extracts A or B.

TABLE C

Comparison of Carotenoid/Chlorophyllin Colloid with Normal Hexane Extraction

|  | Extract A Hexane | Extract B Chl/Hex/3:1 | Extract C Chl/Hex/Eth/ Meth 3:2:1:1 | Wavelength,nm |
|---|---|---|---|---|
| Weight of pigments extracted from 10 g Spirulina | 0.43 g | 0.52 g | 0.81 g | |

TABLE C-continued

Comparison of Carotenoid/Chlorophyllin Colloid with Normal Hexane Extraction

| | Extract A Hexane | Extract B Chl/Hex/3:1 | Extract C Chl/Hex/Eth/ Meth 3:2:1:1 | Wavelength,nm |
|---|---|---|---|---|
| % of pigments and other solubles in 10 g Spirulina | 4.3% | 5.2% | 8.1% | |
| % beta-carotene | 0.23% | 0.60% | 0.73% | |
| 15-cis beta carotene | 20.40% | 20.14% | 19.42% | 425,445,470 |
| all-trans beta carotene | 19.25% | 19.52% | 18.70% | 425,448,476 |
| 9-cis beta carotene | 20.34% | 20.26% | 20.20% | 422,443,470 |
| Not identified I | 19.17% | 19.30% | 20.20% | 416,444,476 |
| Not identified II | 20.84% | 20.70% | 21.48% | 416,438,466 |

After extraction, the carotene-rich solvent is added to a cold starch powder until it is absorbed into a stable carotene colloid with up to 5% carotenoids. The solvent is allowed to evaporate from the starch until all traces of ether and alcohol have been evacuated from the powder. The resulting powder stabilizes the carotene, which can be diluted in absolute alcohol without losing its potency. The powder is settled and the supernatant can then be reconstituted into a carotene polymer with the addition of absolute alcohol in proportion of 30 mg powder to 100 ml alcohol, or down to 10 mg to 100 ml alcohol, depending on concentrations required in the polymer suspension. These dilutions can in turn be used for injections as aqueous dilutions or topical applications without harm to the human body.

The binding capacity of the preferred plant starch polymer, the Instant Gel TM starch polymer (Staley, Inc.), ranges up to 40 mg carotene per gram, or 4% without forming carotenoid crystals, depending on the amount of carotenes placed in the original solvent. Other types of plant starch can bind up to 5% without forming carotene crystals in the solution.

The synergistic or interactive effects of the organic solvent combinations on the proteins and starches of the plant carotenoid source and the consequent destabilization of the natural isomers have generally been ignored. The presence of oxygen, the enzyme oxygenase, methyl groups, and ultraviolet light will cause shifts in the chemistry and stereochemistry of the carotenes, as will temperatures and the pH of the vegetables or algal source. Spirulina protein complexes containing the carotenoids listed in Table A also represent the highest vegetable source of methionine, tyrosine, and tryptophane in foods, and the presence of these components in nature affect the methylation, hydroxylation, and stereomutation of the extracted protein-complexed carotenoids generally. There is evidence to show that by using carotenoproteins as factors to enrich lipo-protein extracts from algae and other vegetable sources of beta-carotene allows carotene precursors and derivatives to form stereochemical associations with other carotenoids. The extracted compounds have also been shown in a related patent application to directly affect animal metabolism in conjunction with the glutathione peroxidase mechanism which controls the evolution of free radicals on cell membranes. The extracts have also been shown to directly trigger macrophage production of tumor necrosis factor (TNF). It is suggested by current research that certain carotenoids may play a vital role in the respiratory chain of neurones and act in the cell oxidation of plants and animals. In particular, the concentration of carotenoids and calcium ions in mitochondria, complex isoprenoid molecules, and other carotenoid containing membranes suggests that carotenoids, in addition to their anti-oxidant functions, also play a role in regulating the transfer of calcium ions across membranes.

The organic solvent mixture employed herein allows extraction of chlorophylls and tetrapyrroles from the species *Dunaliella salina*, including up to 10% beta-carotene. The present extraction process used on Spirulina yields similar proportions of carotenoid isomers, as shown in Table I and in Table II to follow.

TABLE I

Comparison between Synthetic Beta-Carotene and Natural Beta-Carotene from Spirulina and *Dunaliella bardawil*

| | | | | % Natural Beta-Carotene | |
|---|---|---|---|---|---|
| Isomer | Absorption maxima (nm) | % Synthetic Beta-Carotene | % Vitamin A Activity | Spirulina | *Dunaliella bardawil* |
| 15-cis | 425 | | | | |
| | 445 | 17% | 93% | 20.4% | 10% |
| | 470 | | | | |
| All-trans | 425 | | | | |
| | 448 | 78% | 100% | 19.25% | 42% |
| | 476 | | | | |
| 9-cis | 443 | | | | |
| | 470 | 4% | 22% | 20.34 | 41% |
| | 328 | | | | |

TABLE II

Comparison of Yields of Algal Carotene Isomers

| | | | | Spirulina | |
|---|---|---|---|---|---|
| Isomer | Absorption maxima (nm) | Prior Art for *D. bardawil* | *D.salina* Corn Oil Process | Hexane Process | CHL/Hex 3:1 Process |
| 15-cis | 425 | | | | |

TABLE II-continued

Comparison of Yields of Algal Carotene Isomers

| Isomer | Absorption maxima (nm) | Prior Art for D. bardawil | D.salina Corn Oil Process | Spirulina Hexane Process | CHL/Hex 3:1 Process |
|---|---|---|---|---|---|
| All-trans | 445 470 425 | 10% | 20.6% | 20.4% | 20.19% |
| 9-cis | 448 475 422 | 42% | 20.1% | 19.25% | 19.52% |
| Unidentified | 443 470 416 | 41% | 20.86% | 20.34% | 20.26% |
| Unidentified | 444 476 416 | 5% | 18% | 19.17% | 19.3% |
|  | 438 466 | 1% | 20.44% | 20.84% | 20.7% |

The particular conjugations of protein and starch extracted from these algae and other vegetable sources of carotene and chlorophyll pigments are enriched when dissolved and then redried in an oxygen-free environment onto an instant-starch base, and reconstitute as a colloid with wide spectrum of carotenes, tetrapyrrole pigments, and prophyrins as close to the natural proportions as possible. The process allows interactions with isomers different from those of synthetic beta-carotene or from those of natural beta-carotene extracted by hexane, because it reduces the changes caused by solvents interacting with plant starch, proteins, and nucleic acids with the application of heat at temperature over 70° C. It is well known that in nature plants and bacteria produce carotenes whose carotene isomers are directly adapted by temperatures and light in the presence of certain amino acids such as tryptophane and tyrosine. Since Spirulina is high in tryptophane and tyrosine, a cold process for complexing the water-soluble proteins with these carotenoids is preferable in order to retain the singlet oxygen-quenching effect on cell membranes.

The synthetic beta-carotene commercially available has been converted to the all-trans isomer in the accepted prior understanding that the effectiveness as Vitamin A of naturally occurring betacarotene is mostly due to the all-trans, which converts to 100% activity of Vitamin A. The 9-cis form converts to 19% Vitamin A. However, experiments have shown that it is not Vitamin A which has enhanced the immune system and which has a regressive and destructive effect on cancer tumors, but the natural beta-carotene itself applied along with other protein-bonded pigments in solution directly to tumor cells. The particular isomer of betacarotene and the way it combines with other naturally-occurring isomers is separated as a function of the solvent mix and the heat treatment in the normal extraction process. There exists a need for a new process that will enable not only beta-protein carotenoid-complex colloid, along with other natural water-soluble extracts found complexed together with these carotenoid in their natural state. This need for a cold process to produce a water-soluble beta-carotene and other carotenes from natural sources has never been met as the technology for preparing beta-carotene in aqueous solutions suitable for medical applications has not yet been available. Hence, the invention relates to a novel process for the preparation of water-soluble and water-dispersible carotenoids. By combination of certain organic solvents in the correct proportions, a soluble extract carotenoid complex from lipoproteins, consisting of a protein conjugated with several carotenoids, is blended together with a water-soluble protein-starch extract of the tetrapyrrole pigments and porphyrins.

The invention is illustrated further by the following examples.

EXAMPLE 1

Water-soluble extracts of phycocyanin and other porphyrins were obtained from 10 g Spirulina by the following method.

The grams of Spirulina were extracted in distilled water for 3 hours at 25° C., and further extracted in refrigerator for 2 weeks, then separated from the phycocyanin extract and centrifuged at 3500 rpm for 5 minutes. The phycocyanin extract still contains chlorophyll (a) particles of less than 5-micron size. The extract was dried at 45° C.

Dry phycocyanin powder obtained = 5.474 g/10 g Spirulina.

Dry Spirulina residue = 4.525 g.

That is, 54.75% of the 10 g of Spirulina was leached into the water during the extraction process.

In blue-green algae, the phycocyanins constitute as much as 40% of their total soluble proteins.

In Spirulina, both c-phycocyanin and allophycocyanin are present. C-phycocyanin constitutes almost 22% of the total protein in Spirulina.

The above extract can be reconstituted at any time from the dried concentrate merely by adding it to water in any strength desired or, alternatively, adding it to the water soluble carotenoid extracts. (See Example 2)

EXAMPLE 2

The vegetable algae Spirulina containing the carotenoids was ground up, breaking and disintegrating the cells to release the globules of oil. After filtration, a premixed organic solvent was used on the residue with 3 parts chloroform, 3 part hexane, 1 part ether, and 1 part methyl alcohol, and many kinds of crystals of carotenoids are recovered from the solvent by conventional means.

The crystals from the solvent were then dissolved in 1 part ether and 9 parts absolute alcohol, and mixed with dry granular instant-starch gel powder (Instant gel ™, Staley, Inc.) to form a colloid solution for 10 minutes, then dried so that the ether and alcohol were recovered, leaving the dry starch powder grains.

The dried water-soluble filtrate powder was mixed with the instant starch grains of carotenoids in order to form a wide spectrum of oil-soluble carotenoid pigments and water-soluble powder pigments in dry form. This final product in powder form can then be stored or transported for use in the following way:

At the time of use and according to the concentration needed, 10% to 30% of the powder is placed in absolute alcohol and shaken for as long as 2 hours, or longer as desired. The solids are then allowed to settle over 24 hours, and the resulting supernatant colloid polymer can be used by dilution in water as an injectable product, an intravenous drip, a topical application, or an oral mouthwash, or in drinks or foods for nutritional purposes.

EXAMPLE 3

A filtrate containing water-soluble pigments (prepared as in Example 1) was blended with water and starch and settled to let the solids precipitate. The resulting strata of colors in the supernatant were syphoned off separately and were allowed to form a water-soluble powder by slowly drying at a temperature of 70° C., or freeze dried. This treatment of the filtrate resulted in a water soluble powder extract of pigments and proteins consisting of about 54% of total. These water soluble pigments and protein complexes were then combined with the carotenoid preparation of Example 2 to make a compound extract.

EXAMPLE 4

Algal material was washed and dewatered by belt filter or vacuum filter to remove any salts or medium used in the growing process. The material was disintegrated to provide an emulsion. After adjusting pH to 2.5 with a food grade acid, the mixture was heated for 2 hours to 70° C. using 10% to 25% soy, palm, corn or fish oil as an extraction vehicle or solvent. During this mild heating, the algal material was kept circulating through the solvent tank by a homogenizing pump. The resulting mix was allowed to stand for 2 hours and to cool down to room temperature. After centrifugation in an oil-refining or cream separator, the pigments were recovered in concentrated form in the oil and packaged as carotenoid extract yielding 0.15% to approximately 1.8% carotene.

I claim:

1. A method of preparing a water soluble extract of carotenoid pigments from vegetable material containing such pigments, comprising the steps of:
   a. extracting the vegetable material with a nonpolar organic solvent to remove the pigments;
   b. separating the solvent from vegetable material;
   c. absorbing the solvent containing the pigments into a vegetable starch;
   d. allowing the solvent to evaporate from the starch;
   e. precipitating the starch in alcohol; and
   f. recovering the resulting supernatant containing the pigments.

2. A method of claim 1, wherein the vegetable material is algae of the genera Spirulina or Dunaliella.

3. A method of claim 1 wherein the solvent is a mixture of chloroform:hexane:ether:methanol in proportions of about 3:2:1:1.

4. A method of claim 1, wherein the starch is a pregelatinized corn starch.

5. A method of claim 1, wherein the vegetable material is algae.

6. A method of claim 1, wherein the nonpolar organic solvent contains a polar component.

7. A method of preparing a water soluble extract of carotenoid pigments from algae containing such pigments, comprising the steps of:
   a. extracting disintegrated algae with organic solvent mixture comprising chloroform:hexane:ether:methanol in proportions of about 3:2:1:1;
   b. removing the algae residue from the solvent mixture;
   c. absorbing the solvent mixture onto a pregelatinized vegetable starch;
   d. allowing the solvent mixture to evaporate from the starch; and
   e. precipitating the starch in alcohol; and
   f. recovering the resulting alcoholic supernatant containing water soluble carotenoids.

8. A method of producing a composite water soluble extract of carotenoid, tetrapyrrole and porphyrin pigments from vegetable sources of such pigments, comprising the steps of:
   a. preparing a water extract of a vegetable material by:
      (i) lysing the cells of a vegetable material;
      (ii) extracting the vegetable material in buffered, distilled water; and
      (iii) removing the vegetable residue from the water and drying the water extract to obtain a powder of water extracted pigments;
   b. preparing a water-soluble extract of carotenoid pigments by:
      (i) extracting vegetable material with a solvent comprising a non-polar organic solvent to remove carotenoid pigments;
      (ii) separating the solvent from the vegetable material;
      (iii) absorbing the solvent containing the pigments into a vegetable starch;
      (iv) allowing the solvent to evaporate from the starch;
      (v) precipitating the starch in absolute alcohol; and
      (vi) separating the resulting alcoholic supernatant containing the pigments and drying the supernatant to form a powder of water soluble carotenoid pigments; and
   c. combining the powders of steps a and b to form a composite extract.

9. A method of claim 8, wherein the vegetable material is algae of the general Spirulina or Dunaliella.

10. A method of claim 8 wherein the solvent is a mixture of chloroform:hexane:ether:methanol in proportions of about 3:2:1:1.

11. A method of claim 8, wherein the starch is a pregelatinized corn starch.

* * * * *